(12) United States Patent
Kocagoz

(10) Patent No.: US 7,754,485 B2
(45) Date of Patent: Jul. 13, 2010

(54) CULTURE MEDIUM FOR RAPID DETECTION OF MYCOBACTERIAL GROWTH BY COLOR CHANGE

(75) Inventor: Tanil Zuhtu Kocagoz, Istanbul (TR)

(73) Assignee: Salubris, Inc., Woburn, MA (US)

( * ) Notice: Subject to any disclaimer, the term of this patent is extended or adjusted under 35 U.S.C. 154(b) by 799 days.

(21) Appl. No.: 10/683,565

(22) Filed: Oct. 10, 2003

(65) Prior Publication Data

US 2005/0079570 A1 Apr. 14, 2005

(51) Int. Cl.
*C12N 1/20* (2006.01)
*C12N 1/00* (2006.01)
*C12N 5/02* (2006.01)

(52) U.S. Cl. .................... 435/404; 435/243; 435/252.1; 435/253.1

(58) Field of Classification Search ................. 435/243, 435/252.1, 253.1, 404
See application file for complete search history.

(56) References Cited

U.S. PATENT DOCUMENTS 6,197,574 B1 * 3/2001 Miyamoto et al. ....... 435/287.6

2001/0055787 A1 * 12/2001 Heifets et al. ................. 435/32

FOREIGN PATENT DOCUMENTS

WO WO 00/15045 * 3/2000

OTHER PUBLICATIONS http://www.bd.com/ds/technicalCenter/inserts/Middlebrook_7H10_Agar.pdf.*

* cited by examiner

*Primary Examiner*—Ruth A Davis

(57) ABSTRACT

The diagnosis of mycobacteria may be made by growing bacteria from clinical samples in a culture media. The culture medium enables rapid detection of mycobacterial growth by changing its color. It also differentiates mycobacterial growth from contamination by changing to a different color when other species of microorganisms grow. Different types of culture media may be obtained by adding antimicrobial drugs to either obtain a medium selective for mycobacteria or a medium for species differentiation or susceptibility testing of drugs.

1 Claim, No Drawings

US 7,754,485 B2

CULTURE MEDIUM FOR RAPID DETECTION OF MYCOBACTERIAL GROWTH BY COLOR CHANGE

BACKGROUND

1. Field of Invention

The present invention generally relates to a method and composition for the detection of bacteria. More particularly, the invention relates a method and composition for the rapid detection of mycobacteria.

2. Description of Related Art

Tuberculosis continues to be a major health problem around the world. It is estimated that every year ten million people become tuberculosis patients and three million die of this disease. Definitive diagnosis of tuberculosis typically requires isolation of *Mycobacterium tuberculosis*, or other species of mycobacteria that may cause similar diseases, from patients' clinical samples grown in microbiological culture media. Obtaining pathogenic mycobacteria as pure culture is also important in determining its susceptibility to antituberculosis drugs.

In conventional mycobacterial culture media, the growth of mycobacteria is detected by visualization of colonies formed by mycobacteria, which generally requires 3 to 8 weeks. To shorten the duration of time required for growth detection, several rapid mycobacterial culture systems using Middlebrook liquid medium have been developed. These systems have disadvantages, however, such as using radioactive substances, requiring expensive equipment and/or having difficulties in application.

One of the oldest and most widely used rapid detection systems is the radiometric culture system in which mycobacterial growth is monitored by the formation of radioactive $CO_2$ from $^{14}C$ labeled palmitic acid included in the Middlebrook media. This method has the major disadvantage of using radioactive chemicals that requires the disposal of culture bottles using special precautions.

More recently, a fluorometric system has been developed in which mycobacterial growth is monitored by a decrease in oxygen and formation of $CO_2$ that reduces an indicator embedded in a gel at the bottom of the tube. Reduction of the indicator causes the indicator to fluoresce when activated by UV light. The culture tubes may be evaluated either visually using a UV light source or by an automated instrument.

In another system carbon dioxide released into liquid Middlebrook medium by actively growing mycobacteria is detected through a colorimetric indicator embedded in a gel at the bottom of culture vials. Color changes are monitored by a reflectometric detection unit.

Another system is based on detection of pressure changes resulting from gas production or gas consumption in the headspace of the culture bottle. Although the growth detection principles, in the rapid culture systems described above, are different, they all contain modified types of Middlebrook medium in culture vials. With these systems, it is not possible to differentiate mycobacterial growth from contamination without doing microscopy or further tests.

SUMMARY

Described herein is a new culture medium that enables the rapid detection of mycobacterial growth by monitoring the color of the culture medium.

In one embodiment, a culture medium changes its color (e.g., red to yellow) when mycobacteria start to grow. This induced color change at the onset of mycobacterial growth may allow early detection of growth by eliminating the necessity of waiting for visible colonies to form in the medium as is typically done in conventional media. Further, the color of the medium changes its color to a different color (e.g., from red to green) when species other than mycobacteria grow. This property of the medium may allow differentiation of contamination from real mycobacterial growth. Addition of antibacterial compounds into the TK medium allows rapid susceptibility testing and typing of the mycobacteria present.

DETAILED DESCRIPTION

In one embodiment, a medium for growth and detection of mycobacteria is composed of a mixture that induces growth of the mycobacteria. The medium also includes an indictor. The indicator is selected to undergo a color or fluorescent change as the mycobacteria grow. In one embodiment, growth of the mycobacteria alters the pH of the medium. The indicator presence in the medium may undergo a change of color or fluorescence in response to the pH change of the medium. In this manner the presence of mycobacteria in the medium can be rapidly determined.

In one embodiment, a medium, referred to herein as "TK medium" includes a magnesium salt, an iron salt, an amino acid, a carbohydrate, an indicator, a dye and a gelling substance. The selection of these chemicals is chosen to promote growth of mycobacteria such that the pH of the medium is altered as the mycobacteria grow. The indicator is chosen to undergo a color or fluorescent change as the pH of the medium is altered.

The medium may include one or more magnesium compounds. Magnesium compounds that may be used include water-soluble magnesium salts (e.g. magnesium sulfate). Magnesium salts may be present in an amount ranging from 100 to 1000 mg per liter.

The medium may include one or more iron compounds. Iron compounds that may be used include water-soluble iron salts (e.g., ferric ammonium citrate). Iron salts may be present in an amount ranging from 100 to 1000 mg per liter.

The medium may include one or more amino acids. Any of the naturally occurring amino acids may be used. In some embodiments, amino acids with acidic side chains may be used. Examples of amino acids with acidic side chains include L-glutamic acid and L-aspartic acid. Amino acids may be present in an amount ranging from about 0.5 to 5.0 g per liter The medium may also include one or more carbohydrates (e.g., glucose). Carbohydrates may be present in an amount ranging from 1.0 to 10.0 g per liter.

The medium may also include an indicator. Any indicator may be used that undergoes a change in a spectroscopic property when the pH of the medium changes due to the growth of mycobacteria. Spectroscopic changes include changes in the color and/or fluorescence of the indicator. The indicator should be selected such that a detectable change in the spectroscopic properties of the indicator occur when mycobacteria grow in the medium. The medium may have a starting pH. At the starting pH, the indicator may exhibit a first spectroscopic property (e.g., a first color). When a sample is added to the medium, growth of mycobacteria may begin, if mycobacteria are present in the sample. The growth of mycobacteria will begin to alter the pH of the medium. As the pH of the medium is altered, a spectroscopic property of the indicator may change such that the indicator exhibits a second spectroscopic property that is different from the first spectroscopic property (e.g., a second color). In this manner, the indicator may allow the rapid determination of the presence of mycobacteria. Examples of indicators that are particularly useful for the determination of mycobacteria include, but are not limited to, bromophenol blue, methyl red, phenol red, and bromocresol purple. Each of these indicators may exhibit color changes when mycobacteria begins to grow in the medium. Other indicators may also be chosen, depending on the pH of the medium and the expected change in pH due to growth of mycobacteria. Indicators may be present in a range from about 10 to 200 mg per liter.

The medium may also include one or more inhibitors. An inhibitor inhibits the growth of several species of microorganisms, other than mycobacteria. The use of one or more inhibitors may make the medium more selective for mycobacteria. In one embodiment, the inhibitor may also be a compound that is metabolized by mycobacteria. The inhibitor may serve two purposes. First the inhibitor may inhibit the growth of other bacteria and microorganisms that may interfere with the test. Second, the inhibitor may serve as an additional indicator of the presence of mycobacteria. Some types of bacteria and other organisms may be capable of growing in the medium and altering the pH of the medium, therefore leading to false "positive" test results. The use of an inhibitor like malachite green that is metabolized by mycobacteria (specifically the strain of mycobacteria of interest) may allow an additional test for the presence of mycobacteria. In such a situation, the inhibitor will gradually be destroyed if the mycobacteria is present. If the mycobacteria is not present, but instead some other type of bacteria was present that induced a spectroscopic change of the indicator, the inhibitor will not be destroyed and thus will indicate that the mycobacteria are not present. In some embodiments a dye (e.g., malachite green) may be used as an inhibitor (i.e., the inhibitor may be a colored compound or exhibit a fluorescence). The use of a dye as an inhibitor may be useful for rapidly assessing the presence or absence of the inhibitor using spectroscopic or visual observation. Inhibitors may be present in a range from about 10 to 200 mg per liter.

The medium may optionally include a gelling substance. A gelling substance is added to create a gel-like solid culture medium. Examples of gelling substances include, but are not limited to agar, agarose, gelatin and eggs. A variety of agars may be used as would be know to one of ordinary skill in the art.

The medium may optionally include one or more antimicrobial compounds. In some embodiments, antimicrobial compounds may be added to inhibit the growth of other types of bacteria and/or fungi. Antimicrobial compounds are selected that inhibit other types of bacteria and/or fungi from growing, while allowing mycobacteria to grow. Alternatively, antimicrobial compounds may be used to inhibit various species of mycobacteria from growing. Antimicrobial compounds may be selected that inhibit predetermined species of mycobacteria from growing while allowing other species to grow. In this manner, the medium may be tuned to a specific species of mycobacteria. Additionally, compounds that are known to be antimicrobial pharmaceutical agents with respect to the mycobacteria being studied may be added. The addition of a compound that is effective in the treatment of the specific mycobacetria being studied may be added to test the susceptibility of the isolated mycobacteria to the selected treatment.

EXAMPLES

The TK medium is a new solid culture medium that changes its color (e.g., red to yellow) when mycobacteria start to grow and thus enables early detection of growth by eliminating the necessity of waiting for visible colonies to form on the medium as required in conventional media. The color of the medium changes its color to a different color (e.g., from red to green) when species other than mycobacteria grow and thus enables differentiation of contamination from real mycobacterial growth. Addition of antibacterials into this medium enables rapid susceptibility testing and typing. The TK medium is particularly useful for the detection of mycobacterium tuberculosis.

Preparation of the TK Medium

TK medium includes the following chemicals in the ranges given:

| | |
|---|---|
| Magnesium sulfate.$7H_2O$ | 100-1000 mg |
| Ferric amonium citrate ($Fe^{+2}$) | 100-1000 mg |
| L-Glutamic acid | 0.5-5.0 g |
| D-Glucose monohydrate | 1-10 g |
| Sodium carbonate | 40-400 mg |
| Phenol red | 10-200 mg |
| Malachite green | 10-200 mg |
| Agar | 5-20 g |

The above chemicals are solubilized in 1 liter of deionized water and sterilized by autoclaving to create a liquid medium. During sterilization, an egg is homogenized with an equal amount (about 50 mL) of sterile deionized water. The sterilized liquid medium is cooled down to 40-55° C. and the homogenized egg is added into the medium. The medium is distributed into the tubes and cooled further to create the solid medium.

When mycobacteria grow in TK Medium their metabolic activity creates a pH change of the TK Medium. The initial pH of 7.4 of the medium gradually drops to pH 5.0. The indicator at pH 7.4, which is responsible for the original color of the medium, turns to a different color at pH 5.0 and thus changes the color of the medium. Mycobacteria are organisms that can grow intracellularly. When they enter the body, the pH of the intracellular environment or blood is around pH 7.4. Then, they are phagocytized by macrophages, which are the cells responsible for elimination of any foreign body in the first step of immune system response. In the macrophages mycobacteria are contained in phagosomes for digestion and elimination. Phagosomes contain many hydrolytic enzymes and the pH of their content is around 5.0, which is the optimal pH for the activity of these enzymes. However, mycobacteria can survive in this environment and thus cause infection. The change in the pH in TK Medium during the growth of mycobacteria simulates the body environment and stimulates the growth. In the present example, the indicator will undergo a color change from red to yellow when mycobacteria are growing in the medium.

The dye malachite green serves as an inhibitor that inhibits the growth of several species of microorganisms other than mycobacteria and makes it selective for mycobacteria. When mycobacteria grow, the dye is metabolized by mycobacteria and the color it gives to the medium is eliminated. The final color by mycobacterial growth is obtained by both the color change of the pH indicator and metabolization of the selective dye. However most species that are resistant to the selective dye can grow in TK Medium and cannot metabolize it to eliminate the color it gives to the medium. Thus the final color obtained by the growth of species other than mycobacteria is different than mycobacterial growth. In this way mycobacterial growth can be differentiated from the growth of other contaminant species before confirming by microscopy or other identification methods. In the present example, the color of the dye is green. When metabolized by the mycobacteria the dye becomes colorless. Therefore, a change in color from red to green indicates that the pH of the medium has changed (thus bacterial growth has occurred), however the inhibitor has not been metabolized. Thus the presence of a green color indicates that microorganisms other than mycobacteria have grown in the medium.

In conventional media, the mycobacterial growth is detected by visualization of the colonies forming on the surface. Mycobacterium colonies may become visible in 3 to 8 weeks, depending on the medium used. In TK Medium the color change due to the metabolic activity of growing mycobacteria occurs long before the colonies become visible. The color change of the medium can be followed visually or by an automated instrument.

Other types of TK Medium may be prepared for a variety of applications. Several types of TK Medium for different purposes are obtained by the addition of different types of antimicrobials into the medium.

TK SLC: Selective TK medium allows mycobacteria to grow and inhibits the growth of other bacteria and fungi using five different antimicrobials, (Polymixin B 5 μg/ml, Piperacillin 50 μg/ml, Amphotericin B 25 μg/ml, Nalidixic acid 20 μg/ml, Trimethoprim 2 μg/ml). This medium is used for primary isolation of mycobacteria from clinical samples and the probability of contamination by other microorganisms is lower than TK Medium.

TK PNB: TK Medium containing para-nitro benzoic acid (PNB 750 μg/ml) which contributes to differentiating species belonging to *M. tuberculosis* complex and mycobacteria other than tuberculosis. PNB inhibits the growth of bacteria belonging to the *M. tuberculosis* complex group. (*M. tuberculosis, M. bovis, M. africanum, M. microti*). The growth in TK Medium, but inhibition of growth in TK PNB medium indicates that the isolate belongs to *M. tuberculosis* complex. Growth on both media indicates that the isolate is a mycobacteria other than tuberculosis.

TK Media with antituberculosis drugs: Antituberculosis drugs are added into TK Medium for susceptibility testing of mycobacteria to these drugs. Examples of antituberculosis drugs include, but are not limited to, isoniazid, rifampin, streptomycin, ethambutol, pyrazinamide, amikacin, kanamycin, cycloserine, etionamide, ofloxacin, tiacetazone, para-amino-salicilic acid (PAS) and rifabutine. TK Medium with major antituberculosis drugs that are used primarily in the treatment of tuberculosis are: TK INH (with isoniazid 0.2 μg/ml); TK RIF (rifampin 1 μg/ml); TK STR (streptomycin 2 μg/ml); TK EMB (ethambutol 40 μg/ml). Similarly TK Media with second line antituberculosis drugs can be obtained. Growth on TK Medium and inhibition on a medium containing a drug indicates that the strain is susceptible to this drug. Growth on both media indicates resistance.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A culture medium that indicates the growth of mycobacteria by changing its original color to a different color due to pH created by mycobacterial growth and that identifies contamination by changing its color to a third color due to further change in pH by the growth of organisms of non-mycobacterial origin; comprising: a growth solution, wherein the growth solution is composed of chemicals that promote growth of mycobacteria; one or more indicators, wherein the indicators undergo a spectroscopic change when the pH of the growth solution is altered; and one or more inhibitors, wherein the inhibitors are configured to inhibit growth of microorganisms that are not *mycobacterium*, and wherein the inhibitors undergo a spectroscopic change in the presence of mycobacteria.

* * * * *